United States Patent
Hammes et al.

(10) Patent No.: US 11,752,114 B2
(45) Date of Patent: Sep. 12, 2023

(54) TRANSDERMAL THERAPEUTIC SYSTEM

(71) Applicant: LTS LOHMANN Therapie-Systeme AG, Andernach (DE)

(72) Inventors: Florian Hammes, Andernach (DE); Tobias Kleudgen, Ettringen (DE); Anja Tomeleri, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 16/386,458

(22) Filed: Apr. 17, 2019

(65) Prior Publication Data

US 2020/0330404 A1 Oct. 22, 2020

(51) Int. Cl.
*A61K 31/135* (2006.01)
*A61K 9/70* (2006.01)
*A61P 25/24* (2006.01)

(52) U.S. Cl.
CPC .......... *A61K 31/135* (2013.01); *A61K 9/7084* (2013.01); *A61K 9/7053* (2013.01); *A61P 25/24* (2018.01)

(58) Field of Classification Search
None
See application file for complete search history.

(56) References Cited

U.S. PATENT DOCUMENTS

| | | | |
|---|---|---|---|
| 6,689,379 B1 * | 2/2004 | Bracht | A61K 9/7061 424/448 |
| 9,962,349 B2 * | 5/2018 | Gennari | A61K 47/10 |
| 2001/0048938 A1 * | 12/2001 | Asmussen | A61K 31/27 424/449 |
| 2002/0192302 A1 * | 12/2002 | Hsu | A61K 38/212 424/719 |
| 2007/0196453 A1 | 8/2007 | Zhang et al. | |
| 2013/0072884 A1 | 3/2013 | Hamlin et al. | |
| 2013/0211351 A1 * | 8/2013 | Fuhrherr | A61K 9/7038 604/307 |
| 2015/0045749 A1 * | 2/2015 | Im | A61P 25/28 604/307 |
| 2018/0064655 A1 | 3/2018 | Yu | |
| 2019/0240167 A1 * | 8/2019 | Verstraelen | A61K 47/32 |

FOREIGN PATENT DOCUMENTS

| | | | |
|---|---|---|---|
| JP | 2003201254 A | | 7/2003 |
| JP | WO2011105486 B2 | | 1/2011 |
| JP | 2012219044 A | | 12/2012 |
| RU | 2484822 C2 | | 6/2013 |
| WO | WO03015699 | * | 2/2003 |
| WO | 2009017767 A2 | | 2/2009 |
| WO | 2009017767 A3 | | 2/2009 |
| WO | 2017003935 A1 | | 1/2017 |
| WO | 2018073227 A1 | | 4/2018 |
| WO | 2018195318 A1 | | 10/2018 |

OTHER PUBLICATIONS

Subedi et al., Influence of formulation variables in transdermal drug delivery systemcontaining zolmitriptan, International Journal of Pharmaceutics 419 (2011) 209-214 (Year: 2011).*
Hai et al., Formulation and biopharmaceutical evaluation of transdermal patch containing benztropine, International Journal of Pharmaceutics 357 (2008) 55-60 (Year: 2008).*
Kim et al., Effect of vehicles and pressure sensitive adhesives on the permeation of tacrine across hairless mouse skin, International Journal of Pharmaceutics 196 (2000) 105-113 (Year: 2000).*
Extended European Search Report for EP Application No. 19169726.7, dated Oct. 2, 2019, 10 pages.
Henkel Ltd., "DURO-TaK and GELVA Transdermal Pressure Sensitive Adhesives DURO-TAK and GELVA Transdermal Pressure Sensitive Adhesives Product Selection Guide", Nov. 20, 2013, Retrived from the Internet, 2 pages.
First examination report of the European Patent Office for Application No. 19169726.7, dated Dec. 20, 2021, 10 pages.
First examination report of the Indian Intellectual Property Office for Application No. 212147051895, dated Dec. 27, 2021, 8 pages.
Office Action for Russian Application 2021133276, dated Jul. 18, 2022, 3 pages.
Henkel Ltd, Duro-Tak and Gelva Transdermal Pressure Sensitive Adhesives Product Selection Guide, Nov. 20, 2013, 2 pages.
Rie Kubota et al., The Development of Transdermal Ketamine Patch, Medical Research Archives, Published Apr. 17, 2018, vol. 6, Issue 4, pp. 2-9.
C. Yang et al., "R-ketamine: a rapid-onset and sustained antidepressant without psychotomimetic side effect", Transi Psychiatry, Sep. 5, 2015, 22 pages.
Office Action for Japanese Patent Application 2021-561657 dated Nov. 22, 2022.

* cited by examiner

*Primary Examiner* — Jennifer A Berrios

(74) *Attorney, Agent, or Firm* — Lippes Mathias LLP (57) ABSTRACT

The present invention concerns a transdermal therapeutic system, comprising a backing layer, which is not permeable for the active ingredient, and a matrix layer on one side of the backing layer, wherein the matrix layer contains at least one pressure sensitive adhesive and ketamine or a pharmaceutically acceptable salt or solvate thereof, wherein the at least one pressure sensitive adhesive has free hydroxyl groups, as well as its use as medicament, in particular for the treatment of depression and pain.

8 Claims, 6 Drawing Sheets

Figure 1A

Minipig plasma level S-ketamine 84h TTS administration time

Figure 1B

Minipig plasma level S-ketamine 24h TTS administration time

TRANSDERMAL THERAPEUTIC SYSTEM

BACKGROUND

The present invention relates to a transdermal therapeutic system (TTS) comprising ketamine as an active ingredient. The invention further concerns the use of such a system as drug, in particular for use in the treatment of depression and/or pain.

In the past years, transdermal therapeutic systems have become increasingly important as dosage form for treating numerous diseases, because they have advantages over common dosage forms. Those are, for example, a precise and constant drug release, which is necessary for a constant concentration of the active ingredient in the blood plasma. Further, the first pass effect can be avoided and compliance can be increased, because the patient does not need to take tablets regularly. An advantage of transdermal therapeutic systems over other topical application systems such as ointments or creams is that they can be applied area accurate and therefore dosage accurate and that there is no risk of incidental wiping off the ointment with contamination of other regions. Further, ointments or tablets must be administered regularly, because a sustained release of the active ingredient usually cannot be achieved otherwise.

A few years ago, it was believed that the implementation of active ingredients in transdermal therapeutic system would be easily achievable, so that this application form would be available for a large number of active ingredients. However, it turned out that this is not correct, because the molecular transport of ingredients via the skin poses a limiting factor. Thus, intense research is always required in order to provide transdermal therapeutic systems for the administration of new active ingredients.

The active ingredient ketamine is long known for the treatment of pain. Recently, it has also been discovered that ketamine is suitable for the treatment of psychological disorders, in particular of depression.

A transdermal therapeutic system provides an attractive option for the administration of ketamine.

Transdermal therapeutic systems for the administration of ketamine are known from the prior art.

For example, WO 2017/003935 A1 and WO 2018/195318 A1 disclose a TTS for the administration of ketamine, wherein a pressure sensitive adhesive is employed, which comprises free carboxyl groups as well as crystallization inhibitors.

However, the TTS for the administration of ketamine known from the prior art require optimization with regard to the flux of the active ingredient and the utilization of the active ingredient contained in the matrix layer. Further it is of advantage to provide formulations in which ketamine is present in a stable form without utilizing crystallization inhibitors.

The present disclosure is directed to a TTS for the administration of ketamine, which has an optimal, such as, as high of a flux of active ingredient as possible, desirably in the first 2 to 12 hours after application, and in which the ketamine contained in the matrix layer is utilized in an optimal manner. Further, the ketamine contained in the TTS can be present under conditions, where it is chemically and physically as stable as possible. Further, the TTS can be simple in design and be economic in its production.

BRIEF DESCRIPTION

Various details of the present disclosure are hereinafter summarized to provide a basic understanding. This summary is not an extensive overview of the disclosure and is neither intended to identify certain elements of the disclosure, nor to delineate scope thereof. Rather, the primary purpose of this summary is to present some concepts of the disclosure in a simplified form prior to the more detailed description that is presented hereinafter.

According to a first embodiment, a transdermal therapeutic system is provided. The TTS includes a backing layer which is not permeable for the active ingredient, and at least one matrix layer on one side of the backing layer. The matrix layer includes at least one pressure sensitive adhesive and ketamine or a pharmaceutically acceptable salt or solvate thereof. The at least one pressure sensitive adhesive comprises free hydroxyl groups.

According to another embodiment, a method of alleviating depression is provided. The method includes the administration of a medicament via a transdermal therapeutic system. The system includes a backing layer which is not permeable for the active ingredient, and at least one matrix layer on one side of the backing layer. The matrix layer includes at least one pressure sensitive adhesive and ketamine or a pharmaceutically acceptable salt or solvate thereof. The at least one pressure sensitive adhesive comprises free hydroxyl groups. The medicament is secured to a patient using the pressure sensitive adhesive.

According to a further embodiment, a method of alleviating pain is provided. The method includes the administration of a medicament via a transdermal therapeutic system. The system includes a backing layer which is not permeable for the active ingredient, and at least one matrix layer on one side of the backing layer. The matrix layer includes at least one pressure sensitive adhesive and ketamine or a pharmaceutically acceptable salt or solvate thereof. The at least one pressure sensitive adhesive comprises free hydroxyl groups. The medicament is secured to a patient using the pressure sensitive adhesive.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

The present disclosure may be understood more readily by reference to the following detailed description of desired embodiments included therein and the accompanying drawings. These figures are merely schematic representations based on convenience and the ease of demonstrating the existing art and/or the present development, and are, therefore, not intended to limit relative size and dimensions of the components thereof.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent can be used in practice or testing of the present disclosure. All publications, patent applications, patents, and other references mentioned herein are incorporated by reference in their entirety. The materials, methods, and articles disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases that require the presence of the named ingredients/steps and permit the presence of other ingredients/steps. However, such description should be construed as also describing compositions, mixtures, or processes as "consisting of" and "consisting essentially of" the enumerated ingredients/steps, which allows the presence of only the named ingredients/steps, along with any impurities that might result therefrom, and excludes other ingredients/steps.

Unless indicated to the contrary, the numerical values in the specification should be understood to include numerical values which are the same when reduced to the same number of significant figures and numerical values which differ from the stated value by less than the experimental error of the conventional measurement technique of the type used to determine the particular value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. The term "substantially" reflects a modification of shape or form that does not effect the necessary function of the associated articles or material.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The present disclosure concerns a transdermal therapeutic system, comprising a backing layer, which is not permeable for the active ingredient, and at least one matrix layer on one side of the backing layer, wherein the matrix layer contains at least one pressure sensitive adhesive and ketamine or a pharmaceutically acceptable salt or solvate thereof, characterized in that the at least one pressure sensitive adhesive comprises free hydroxyl groups.

Generally, the person skilled in the art knows several types of transdermal therapeutic systems. There are DIR (drug-in-reservoir)-systems, comprising a backing layer, a reservoir layer, an adhesive layer and a detachable protective layer. In these systems, the pharmaceutically active ingredient is only present in the reservoir layer, but not in the adhesive layer, which contains at least one adhesive polymer.

Further, DIA (drug-in-adhesive) systems are known, wherein a reservoir layer is omitted and the pharmaceutically active ingredient is present directly in the adhesive layer (also called matrix layer), which contains at least one adhesive polymer.

The advantages of DIA-systems over DIR-systems are among others a simpler production process and a lower risk of abuse. The lower risk of abuse is highly relevant in particular with regard to the active ingredient ketamine.

Thus, the transdermal therapeutic system according to the present disclosure can be a DIA-system. That is, the active ingredient, ketamine or a pharmaceutically acceptable salt or solvate thereof, can be present jointly with the at least one pressure sensitive adhesive in one and the same layer.

Such a TTS is characterized by its relatively simple design and thus by an economically advantageous production. Further, such a TTS according to the present disclosure has a higher flux of active ingredient compared to known TTSs comprising pressure sensitive adhesives which do not comprise free hydroxyl groups. As is commonly known, a hydroxyl-group and a hydroxy-group, respectively is a —OH group. The ketamine contained in the matrix layer can be utilized in an optimal manner.

The TTS according to the present disclosure has a high skin tolerance.

The term "utilized in an optimal manner" denotes that the ketamine contained in the matrix layer diffuses from the matrix layer into the skin of the patient to the widest possible extent during the application of the TTS on the patient's skin so that after application as little "unutilized" active ingredient remains in the matrix layer as possible.

The term "backing layer, which is not permeable for the active ingredient," denotes that the backing layer is substantially, or even completely, impermeable for the active ingredient ketamine.

Suitable materials for the backing layer comprise materials such as polyester, e.g. polyethylene terephthalate, polybutylene terephthalate, polyethylene napthalate, polyolefines, such as polyethylene or polypropylene, ethylene-vinyl acetate, polyvinyl chloride, polyamide (Nylon) and/or polyurethane. The backing layer can also be composed of a composite material or an aluminum film coated with one of the above materials.

A pressure sensitive adhesive can be a polymer, which itself acts as pressure sensitive adhesive, as defined in DIN EN 923:2016-03.

Ketamine is (S)-(+)-2-(2-chlorophenyl)-2-(methylamino)cyclohexan-1-one ((S)-ketamine), (R)-(−)-2-(2-chlorophenyl)-2-(methylamino)cyclohexan-1-one ((R)-ketamine) as well as the racemate (RS)-(±)-2-(2-chlorophenyl)-2-(methylamino)cyclohexan-1-one. Pharmaceutically acceptable salts and solvates of these compounds are also suitable. Mixtures of these compounds are similarly suitable. One exemplary salt is ketamine·HCl.

The at least one pharmaceutically active ingredient in the transdermal therapeutic system can be (S)-ketamine and/or a pharmaceutically acceptable salt or solvate thereof. (S)-ketamine·HCl is one example.

The at least one pressure sensitive adhesive of the present transdermal therapeutic system can comprise an acrylic copolymer comprising free hydroxyl groups.

The at least one pressure sensitive adhesive can comprise an acrylic copolymer selected from 2-ethylhexyl acrylic acetate, vinyl acetate, and 2-hydroxyethyl acrylate comprising free hydroxyl groups.

Surprisingly, it has been found that the use of such copolymers in the matrix layer effects a high flux of active ingredient and the utilization of the ketamine contained in the matrix layer in an optimal manner.

Further, it has surprisingly been found that the transdermal therapeutic system according to the present disclosure has a sufficient adhesive strength, although the use of matrix polymers and in particular of acrylate polymers comprising carboxyl groups, which are renowned for a high adhesiveness, are avoided.

Suitable pressure sensitive adhesives are known under the trade name DURO-TAK, in particular DURO-TAK 87-4287, DURO-TAK 87-2516, DURO-TAK 2287 or DURO-TAK 2510 and are available from Henkel, Germany.

Since the presence of free carboxyl groups can reduce the flux of the active ingredient and the related absorption of the active ingredient, the transdermal therapeutic system according to the present disclosure can employ at least one pressure sensitive adhesive containing less than 4 wt. % carboxyl groups, more preferred in a range of 1 to 3% and even more preferred less than 1% or at least substantially no free carboxyl groups or no free carboxyl groups.

Further, the transdermal therapeutic system according to the present disclosure can include at least one pressure sensitive adhesive having free hydroxyl groups obtained without the substantial use of a crosslinking agent, or without a crosslinking agent.

A crosslinking agent is a chemical compound which can effect a higher cohesion and a higher firmness of single layers of the therapeutic system. Such crosslinking agents commonly comprise metal chelates.

Omitting the crosslinking agent during the production of the pressure sensitive adhesive may also increase the flux of the active ingredient.

Further, the transdermal therapeutic system according to the present disclosure can include at least one pressure sensitive adhesive having free hydroxyl groups obtained with the use of a crosslinking agent.

A crosslinking agent is a chemical compound which can effect a higher cohesion and a higher firmness of single layers of the therapeutic system. Such crosslinking agents commonly comprise metal chelates.

The use of a crosslinking agent during the production of the pressure sensitive adhesive may also increase the flux of the active ingredient.

Further, the transdermal therapeutic system according to the present disclosure can include at least one pressure sensitive adhesive comprising free hydroxyl groups constituting about 60 to 90 wt.-%, or about 70 to 85 wt.-%, of the weight of the entire matrix layer.

Further, the transdermal therapeutic system according to the present disclosure can include a matrix layer comprising at least one penetration enhancer.

The at least one penetration enhancer is a compound which stabilizes the active ingredient in dissolved form and thus provides a relatively high and over a long term stable resorption of the active ingredient via the skin. The term "penetration enhancer" thus may be replaced by the term "solubilizer".

The penetration enhancer can be selected from carboxylic acids, fatty acids, and/or fatty acid esters, such as levulinic acid, valeric acid, hexanoic acid, caprylic acid, nonanoic acid, decanoic acid, lauric acid, myristic acid, palmitic acid, stearic acid, arachidic acid, behenic acid, lignoceric acid, 3-methylbutanoic acid, neoheptanoic acid, neononanic acid, isostearic acid, oleic acid, palmitoleic acid, linolenic acid, vaccenic acid, petroselinic acid, elaidic acid, oleic acid, arachidonic acid, gadoleic acid, erucic acid, methyl propionate, methyl valerate, diethyl sebacate, methyl laurate, ethyl laurate, ethyl oleate, isopropyl decanoate, isopropyl myristate, isopropyl palmitate, and/or isopropyl oleate.

Compounds such as diethyltoluamide (DEET), propylene glycol monocaprylate, propylene glycol, polyethylene glycol, diisopropyl adipate, eugenol, transcutol, lauryl lactate and/or oleyl alcohol are also suitable as a penetration enhancer.

The transdermal therapeutic system according to the present disclosure can include at least one penetration enhancer selected from levulinic acid and/or methyl laurate.

The at least one penetration enhancer can comprise one of levulinic acid and methyl laurate or a mixture of levulinic acid and methyl laurate.

Further, the transdermal therapeutic system according to the present disclosure can include the at least one penetration enhancer in the matrix layer in an amount of about 1 to 15 wt.-%, or about 4 to 10 wt.-%, based on the weight of the matrix layer.

The application time, which is intended for the transdermal therapeutic system can at least about 6 hours, or at least about 12 hours, or at least about 24 hours. The amount of active ingredient can be adapted to the desired application time.

The transdermal therapeutic system according to the present disclosure can contain ketamine in the matrix layer in an amount of about 1 to 25 wt.-%, or about 5 to 15 wt.-%, based on the weight of the matrix layer.

The transdermal therapeutic system according to the present disclosure can include at least one antioxidant in the matrix layer.

The at least one antioxidant is a chemical compound which prevents or reduces the oxidation of other substances, in particular of the active ingredient, and thus acts against aging of the therapeutical system. In particular, antioxidants are characterized by their effect as radical scavengers and by that they prevent oxidative decomposition of sensitive molecules, in particular of the active ingredient, effected by oxygen in the air. The at least one antioxidant can be selected from the group consisting of alpha-tocopherol, ascorbyl palmitate, dibutylhydroxytoluene and mixtures thereof.

The transdermal therapeutic system according to the present disclosure can contain the at least one antioxidant in the matrix layer in an amount of about 0.001 to 5 wt.-%, or about 0.01 to 2 wt.-%, based on the entire weight of the matrix layer.

Apart from the above mentioned components, the matrix layer may further include common additives. According to their function, these can be classified as softeners/plasticizers, tackifiers, stabilizers, carriers and/or fillers. The relevant, physiologically uncritical, substances are known to the person skilled in the art.

The softener/plasticizer may be selected from linear or branched, saturated or unsaturated alcohols having 6 to 20 carbon atoms, triglycerides and polyethylene glycols.

The tackifier may be selected from triglycerides, dipropylene glycol, resins, resin esters, terpenes and derivatives thereof, ethylene vinyl acetate adhesives, dimethylpolysiloxanes and polybutenes.

The stabilizer may be selected from tocopherol and ester derivatives thereof and ascorbic acid and ester derivatives thereof specific examples include ascorbyl esters of fatty acids and tocopherol, and ascorbyl palmitate or α-tocopherol.

Carriers and/or fillers such as silica gels, titanium dioxide and zinc oxide may be used in conjunction with the polymer in order to influence certain physical parameters, such as cohesion and bond strength, in the desired way.

Further, abuse deterrent agents can be added to the transdermal therapeutic system to prevent or at least reduce its abuse potential. Examples for substances that can be employed as abuse deterrent agents are bittering agents, gel forming agents, irritants, substances leading to acute gastrointestinal, cardiac or respiratory effects, substances leading to violent nausea or vomiting, substances leading to repugnant smells, substances inducing sleep, substances leading to deactivation or degradation of the active ingredient upon attempted extraction.

Further, the transdermal therapeutic system can also comprise an abuse deterrent feature that renders the active and/or the system ineffective when it is used in any other way than its intended use, i.e. transdermal application.

Further, additional active ingredients can be added to the transdermal therapeutic system either to counteract potential adverse effects of ketamine or to enhance the effects of ketamine. Additional active ingredients can be selected from the group of nonsteroidal anti-inflammatory drugs (NSAIDs, e.g. ibuprofen, ketoprofen, meloxicam, piroxicam, indomethacin), COX-2 inhibitors (e.g. celecoxib, etoricoxib), opioids (e.g. fentanyl, buprenorphine, morphine, codeine, oxycodone, hydrocodone, dihydromorphine, pethidine), MAOIs (irreversible and nonselective, e.g. phenelzine, tranylcypromine, isocarboxazid), MAOIs (reversible inhibitor of MAO-A, e.g. moclobemide), MAOIs (preferential inhibitor of MAO-B, e.g. deprenyl), tricyclic (and tetracyclic) antidepressants (e.g. clomipramine, imipramine, amitriptyline, nortriptyline, protriptyline, maprotiline, amoxapine, doxepin, desipramine, trimipramine), selective serotonin reuptake inhibitors (e.g. fluoxetine, sertraline, paroxetine, fluvoxamine, citalopram, escitalopram), selective noradrenaline reuptake inhibitors (e.g. reboxetine, atomoxetine), noradrenaline and dopamine reuptake inhibitor/releaser (e.g. bupropion), serotonin and noradrenaline reuptake inhibitors (e.g. venlafaxine, milnacipran, duloxetine), serotonin antagonists/reuptake inhibitors (e.g. nefazodone, trazodone), alpha2-adrenoceptor antagonist (e.g. mirtazapine) and mixtures thereof.

The matrix layer of the transdermal therapeutic system according to the present disclosure can have an area weight of about 30 to 400 g/m$^2$, or about 100 to 275 g/m$^2$.

The transdermal therapeutic system according to the present disclosure is further characterized in that the transdermal therapeutic system comprises a detachable protective layer on the side of the matrix layer on which the backing layer is not arranged.

The detachable protective layer, which is in contact with the matrix and which is detached prior to application, comprises for example the same materials as used for the production of the backing layer, provided that they are made detachable, e.g. by a silicone treatment. Other detachable protective layers are polytetrafluoroethylene, treated paper, cellophane, polyvinyl chloride and the like.

The present disclosure contemplates use of the transdermal therapeutic system as described above as a medicament.

The present disclosure contemplates use of the transdermal therapeutic system as described above for use in the treatment of major depressive disorder (MDD) (also known simply as depression).

The described transdermal therapeutic systems can be used for the reduction of the suicidal risk and/or the treatment of treatment-resistant depression (TRD).

Major depressive disorder (MDD) is a mental disorder characterized by a pervasive and persistent low mood that is accompanied by low self-esteem and by a loss of interest or pleasure in normally enjoyable activities. Major depressive disorder is a disabling condition that adversely affects a person's family, work or school life, sleeping and eating habits, and general health.

Treatment-resistant depression (TRD) describes a condition that affects people with major depressive disorder (MDD) who do not respond adequately to a course of appropriate antidepressant medication within a certain time.

Further subtypes as recognized by The American Psychiatric Association's Diagnostic and Statistical Manual of Mental Disorders (DSM-5) are melancholic depression, atypical depression, catatonic depression, depression with anxious distress, depression with peri-partum onset and seasonal affective disorder.

The present disclosure also contemplates use of the transdermal therapeutic system as described above for use in the treatment of pain.

Pain is a distressing feeling often caused by intense or damaging stimuli. Pain that lasts a long time is called chronic or persistent, and pain that resolves quickly is called acute.

Nociceptive pain is caused by stimulation of sensory nerve fibers that respond to stimuli approaching or exceeding harmful intensity (nociceptors), and may be classified according to the mode of noxious stimulation. The most common categories are thermal, mechanical and chemical. Some nociceptors respond to more than one of these modalities and are consequently designated polymodal.

Nociceptive pain may be also divided into "visceral", "deep somatic" and "superficial somatic" pain.

Neuropathic pain is caused by damage or disease affecting any part of the nervous system involved in bodily feelings (the somatosensory system). Neuropathic pain may be divided into peripheral, central, or mixed (peripheral and central) neuropathic pain. Peripheral neuropathic pain is often described as "burning", "tingling", "electrical", "stabbing" or "pins and needles".

The transdermal therapeutic systems of the present disclosure can be used in different administration schemes for example in consecutive or staggered administration.

In a consecutive administration transdermal systems are applied in intervals lasting at least 12 h to achieve in the blood plasma of an individual active ingredient concentrations.

Repeated administration can be carried out consecutively without delays, i.e., when the one or more TTSs according to the invention are removed at the end of an application interval, the one or more TTSs according to the invention for the following application interval are applied immediately. The time interval at which there may be no TTSs applied to the body is no more than 10 minutes, or no more than 5 minutes.

In a staggered administration the transdermal systems is applied in intervals lasting at least 4 h to achieve in the blood plasma of an individual active ingredient concentrations.

The staggered administration can be carried out once daily, twice weekly or once weekly, i.e., when the one or more TTSs are removed at the end of an application interval, the one or more TTSs for the following application interval are applied considering a dose free interval of at least 18 hours.

In certain embodiments, all TTSs according to the disclosure are administered on the same skin area of the individual over the total period, i.e., a given skin area of the individual is overlaid or plastered repeatedly with TTSs according to the invention.

In another embodiment, all TTSs according to the disclosure are administered each time on different skin areas of the individual over the total period, i.e., a given skin area of the individual is not overlaid or plastered repeatedly with TTSs.

EXAMPLES

Example 1

The formulations of the S-ketamine-containing coating compositions of Examples 1a-c are summarized in Table 1 below. The formulations are based on weight percent as also indicated in Table 1.

DURO-TAK 387-2052: Pressure sensitive adhesive on the basis of an acrylate vinyl acetate copolymer comprising free carboxyl groups, obtained using a crosslinking agent.

For Examples 1a and 1b, a beaker was loaded with the S-ketamine base and with the solvent (ethyl acetate), and the levulinic acid and the methyl laurate (Example 1b). The acrylic pressure sensitive adhesive polymer DURO-TAK 387-4287 was added and the mixture was then stirred at up to 300 rpm until a homogeneous mixture was obtained (stirring time is about 60 min.).

For Example 1c, a beaker was loaded with the S-ketamine base and with the solvent (ethyl acetate), and the levulinic acid. The acrylic pressure sensitive adhesive polymer (DURO-TAK 387-2052) was added and the mixture was then stirred at up to 300 rpm until a homogeneous mixture was obtained (stirring time is about 60 min.).

For Example 1d, a beaker was loaded with the S-ketamine base and with the solvent (ethyl acetate), and the levulinic acid. The acrylic pressure sensitive adhesive polymer (DURO-TAK 387-2516) was added and the mixture was then stirred at up to 300 rpm until a homogeneous mixture was obtained (stirring time is about 60 min.).

The resulting S-ketamine-containing coating composition was coated on a polyethylene terephthalate film (siliconized, 75 μm thickness, which may function as release liner) and dried for approx. 15 min at room temperature and 15 min at

TABLE 1

| Ingredient (Trade Name) | Ex. 1a Amt [g] | Ex. 1a Solids [%] | Ex. 1b Amt [g] | Ex. 1b Solids [%] | Ex. 1c Amt [g] | Ex. 1c Solids [%] | Ex. 1d Amt [g] | Ex. 1d Solids [%] |
|---|---|---|---|---|---|---|---|---|
| S-ketamine base | 1.20 | 11.90 | 1.00 | 9.97 | 1.20 | 12.02 | 1.00 | 9.96 |
| Acrylic adhesive in ethyl acetate. Solids content of 38.4% by weight (DURO-TAK ™ 387-4287) | 21.17 | 80.52 | 19.29 | 73.62 | — | — | — | — |
| Acrylic adhesive in ethyl acetate. Solids content of 47.5% by weight (DURO-TAK ™ 387-2052) | — | — | — | — | 16.95 | 80.42 | — | — |
| Acrylic adhesive in ethyl acetate. Solids content of 41.9% by weight (DURO-TAK ™ 387-2516) | — | — | — | — | — | — | 20.32 | 84.78 |
| Levulinic acid | 0.77 | 7.58 | 0.62 | 6.17 | 0.76 | 7.56 | 0.53 | 5.26 |
| Methyl laurate | — | — | 1.03 | 10.24 | — | — | — | — |
| Ethyl acetate | 2.09 | — | 3.15 | — | 6.11 | — | 3.22 | — |
| Total | 25.23 | 100.00 | 25.09 | 100.00 | 25.02 | 100.00 | 25.07 | 100.00 |
| Area Weight [g/m²] | 136.5 | | 132.8 | | 130.0 | | 122.8 | |
| S-ketamine content [mg/cm²] | 1.624 | | 1.324 | | 1.562 | | 1.222 | |

DURO-TAK 387-2516: Pressure sensitive adhesive on the basis of an acrylate vinyl acetate copolymer with comprising hydroxyl groups, obtained using a crosslinking agent.

DURO-TAK 387-4287: Pressure sensitive adhesive on the basis of an acrylate vinyl acetate copolymer comprising free hydroxyl groups, obtained without using a crosslinking agent.

60° C. The coating thickness gave an area weight of the matrix layer of 136.5 g/m² (Example 1a), 132.8 g/m² (Example 1b), 130.0 g/m² (Example 1c) and 122.8 g/m² (Example 1d), respectively. The dried film was laminated with a polyethylene terephthalate backing layer (23 μm thickness) to provide an S-ketamine-containing self-adhesive layer structure.

The individual systems were then punched out from the S-ketamine-containing self-adhesive layer structure. In specific embodiments a TTS as described above can be provided with a further self-adhesive layer of larger surface area, preferably with rounded corners, comprising a pressure-sensitive adhesive matrix layer which is free of active agent. This is of advantage when the TTS, on the basis of its physical properties alone, does not adhere sufficiently to the skin and/or when the S-ketamine-containing matrix layer, for the purpose of avoiding waste, has pronounced corners (square or rectangular shapes). The systems are then punched out and sealed into pouches of the primary packaging material.

Preclinical Set Up for the Assessment of Local Tolerance and for the Determination of the Plasma Level of S-ketamine using Ex. 1a, Ex. 1b and Ex. 1d Preclinical Set Up Ex. 1a and Ex. 1d Göttingen minipigs were used in this experiment. Test item formulations and corresponding placebo formulations were tested with a patch application time of 3.5 days (84 hours). Five (5) verum patches and 2 corresponding placebo formulation patches were tested on one animal for each test item formulation.

TTS size: 10 cm$^2$

Preclinical Set Up Ex. 1b

Göttingen minipig was used in this experiment. Test item formulation and corresponding placebo formulation was tested with a patch application time of one day (24 hours). Five (5) verum patches and 2 corresponding placebo formulation patches were tested on one animal.

TTS Size: 10 cm$^2$

The assessment of local intolerance reactions according to DRAIZE (i.e. special emphasis on oedema, erythema or eschar formation) did not reveal any oedemas or erythemas at the application sites of any of the animals treated with the transdermal patches.

No other signs of local intolerance (e.g. discolourations or swellings) were noted for any of the animals at any of the application sites after patch removal.

Figure 1A:
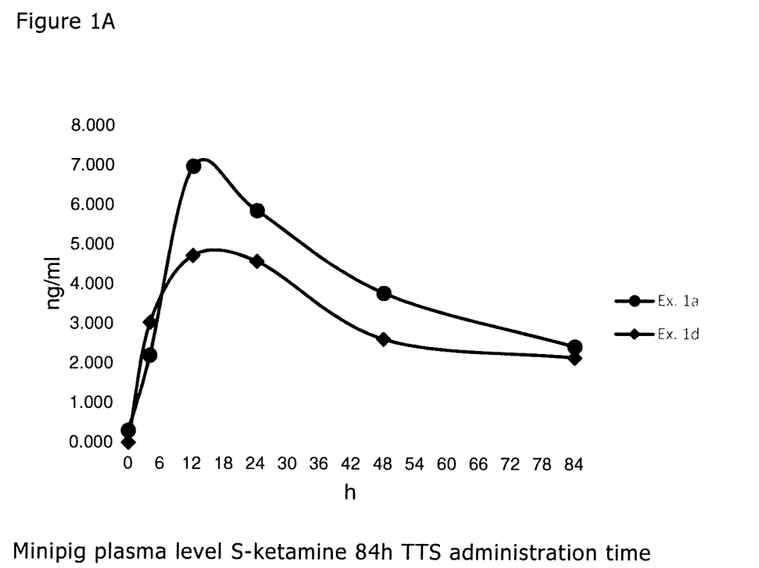
FIG. 1A is a graphical depiction of plasma level S-ketamine 84 hour TTS administration over time and FIG. 1B is a 24 hour illustration.
Figure 1B:
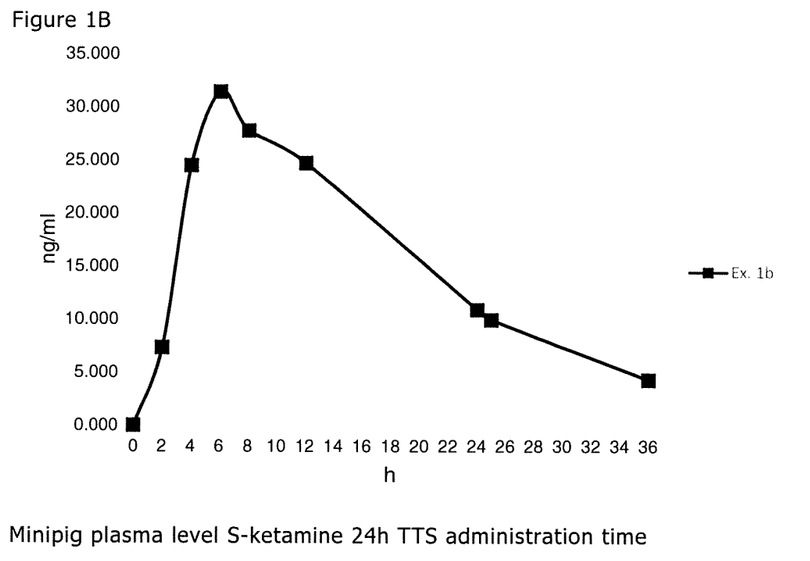

The results for the determination of the plasma level of S-ketamine are shown in FIG. 1.

Measurement of Skin Permeation Rate

The permeated amount and the corresponding skin permeation rates of TTS prepared according to Examples 1a-1c were determined by in vitro experiments in accordance with the OECD Guideline (adopted Apr. 13, 2004) and the EMA guideline on quality of transdermal patches (EMA/CHMP/QWP/608924/2014, adopted Oct. 23, 2014), carried out with a 7.0 ml Franz diffusion cell. Split thickness human abdominal skin (female) was used. A dermatome was used to prepare skin to a thickness of 500 µm, with an intact epidermis for all TTS. Diecuts with an area of 1.152 cm$^2$ were punched from the TTS. The S-ketamine permeated amount in the receptor medium of the Franz cell (phosphate buffer solution pH 5.5 with 0.1% saline azide as antibacteriological agent) at a temperature of 32±1° C. was measured and the corresponding skin permeation rate [µg/cm$^2$*h] is calculated. The results are shown in Table 2 and FIG. 2.

TABLE 2

| | Skin permeation rate with SD [µg/(cm$^2$ h)] | | | | | |
|---|---|---|---|---|---|---|
| Elapsed | Ex. 1a (n = 3) | | Ex. 1b (n = 3) | | Ex. 1c (n = 3) | |
| time [h] | Rate | SD | Rate | SD | Rate | SD |
| 0 | 0 | 0 | 0 | 0 | 0 | 0 |
| 3 | 48.9 | 14.20 | 44.4 | 4.74 | 13.3 | 2.37 |
| 6 | 52.4 | 8.84 | 64.7 | 4.30 | 23.7 | 3.81 |
| 8 | 45.7 | 5.41 | 62.5 | 3.53 | 26.0 | 3.59 |
| 10 | 39.6 | 5.37 | 50.4 | 2.53 | 23.7 | 2.47 |
| 12 | 35.4 | 2.08 | 43.8 | 1.82 | 22.7 | 2.08 |
| 16 | 29.2 | 1.19 | 33.3 | 0.94 | 20.0 | 1.63 |
| 24 | 23.2 | 0.67 | 22.4 | 0.54 | 17.7 | 1.59 |
| 48 | 13.8 | 0.78 | 8.8 | 0.95 | 12.1 | 0.57 |

Utilization of S-ketamine

Figure 3A:
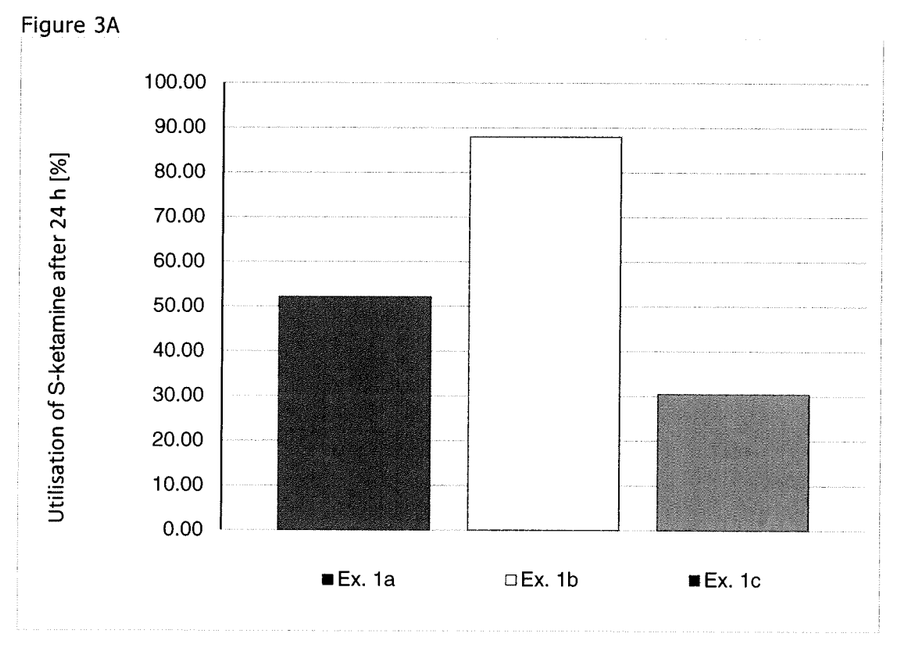
FIG. 3A is a graphical depiction of utilization of S-ketamine after 24 hours and FIG. 3B is after 48 hours.
Figure 3B:
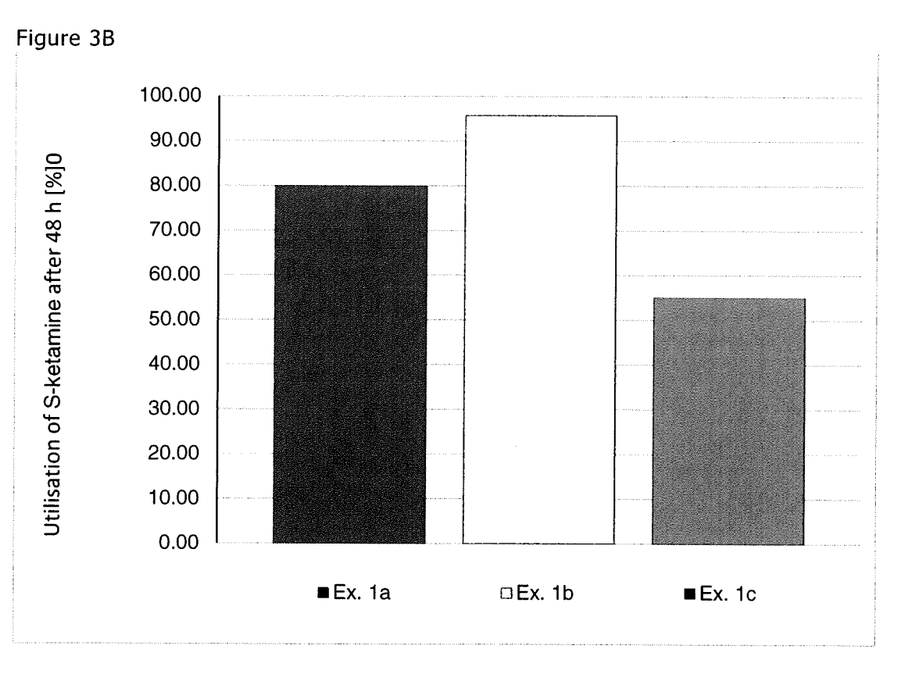

The utilization of S-ketamine at 24 h and 48 h was calculated based on the residual content of the TTS after 24 h and 48 h and the initial S-ketamine content. The results are shown in Table 3 and FIG. 3.

TABLE 3

| Example 1a (n = 3) | Example 1b (n = 3) | Example 1c (n = 3) |
|---|---|---|
| Utilization of S-Ketamine after 24 h [%] | | |
| 52.2 | 88.0 | 30.5 |
| Utilization of S-Ketamine after 48 h [%] | | |
| 79.9 | 95.7 | 55.1 |

Figure 2:
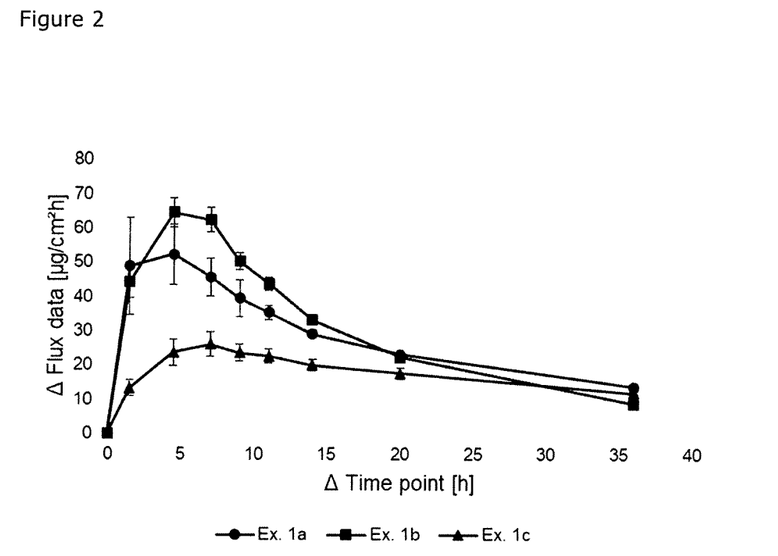
FIG. 2 is a graphical depiction of S-ketamine skin permeation rate.

The results summarized in FIG. 1 to FIG. 3 show an improved utilization of the active ingredient and an improved flux of active ingredient.

Example 2

Comparison of the Skin Permeation using Systems According to the Present Invention and the Prior Art The formulations of the S-ketamine-containing coating compositions of Examples 2a-c were prepared analogously as described in Example 1 and are summarized in Table 4 below. The formulations are based on weight percent as also indicated in Table 4.

TABLE 4

| Ingredient [wt.-%] | Ex. 2a | Ex. 2b | Ex. 2c (Reference Example) |
|---|---|---|---|
| S-Ketamine base | 10.02 | 9.98 | 10.07 |
| DuroTak 87-4287 | 73.97 | 73.83 | — |
| DuroTak 87-4098 | — | — | 54.54 |
| Methyl laurate | 10.04 | 10.10 | — |
| Levulinic acid | 5.97 | 6.09 | 5.14 |
| Eutanol HD | — | — | 5.18 |
| Transcutol | — | — | 5.07 |
| Plastoid B | — | — | 20.00 |
| Area weight [g/m$^2$] | 134.1 | 253.7 | 127.8 |

Figure 4:
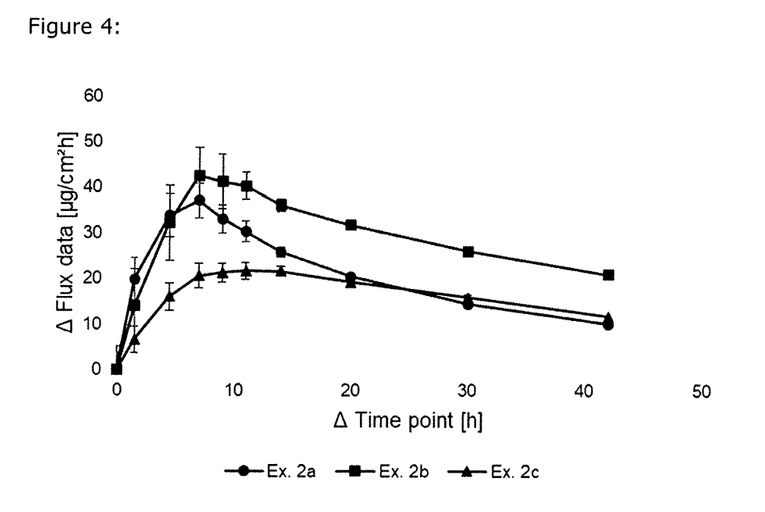
FIG. 4 is a graphical comparison of S-ketamine skin permeation compared to the prior art.

Eutanol HD: Oleyl alcohol (enhancer)
Transcutol: Diethylene glycol monoethyl ether (enhancer)
Plastoid B: Copolymer of butyl methacrylate and methyl methacrylate The skin permeation rate was determined analogously to Example 1 and is summarized in FIG. 4. The skin permeation of the examples is according to the present invention (Ex. 2a and Ex. 2b) advantageous because the onset of the flux (the flux in the first 8 hours) is significantly higher compared to the Reference Example (Ex. 2c).

Example 3

Comparison of the Skin Permeation using Systems According to the Present Invention with Different Coating Weights The formulations of the S-ketamine-containing coating compositions of Examples 3a-c were prepared analogously as described in Example 1 and are summarized in Table 5 below. The formulations are based on weight percent as also indicated in Table 5.

TABLE 5

| Ingredient [wt.-%] | Ex. 3a | Ex. 3b | Ex. 3c |
| --- | --- | --- | --- |
| S-Ketamine base | 10.02 | 10.01 | 10.00 |
| DuroTak 87-4287 | 73.97 | 74.01 | 73.89 |
| Methyl laurate | 10.04 | 9.98 | 10.10 |
| Levulinic acid | 5.97 | 6.00 | 6.01 |
| Area weight [g/m$^2$] | 134.1 | 76.0 | 182.7 |

Figure 5:
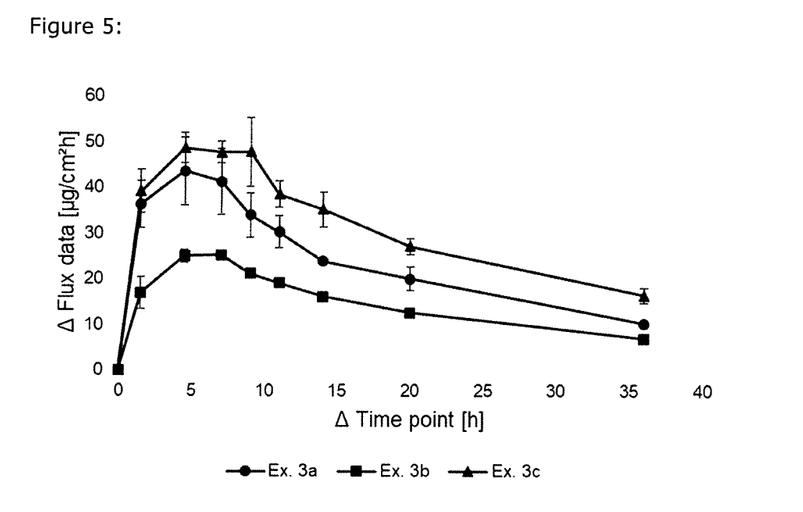
FIG. 5 is a graphical depiction of skin rate permeation rate as a result of coating weight.

The skin permeation rate was determined analogously to Example 1 and is summarized in FIG. 5. The skin permeation of the examples shows the effect of the coating weight on the onset of flux and flux profile.

Example 4

Comparison of the skin permeation using systems according to the present invention with cross linking agent and methyl or ethyl laurate The formulations of the S-ketamine-containing coating compositions of Examples 4a-c were prepared analogously as described in Example 1 and are summarized in Table 6 below. The formulations are based on weight percent as also indicated in Table 6.

TABLE 6

| Ingredient [wt.-%] | Ex. 4a | Ex. 4b | Ex. 4c |
| --- | --- | --- | --- |
| S-Ketamine base | 10.02 | 9.96 | 10.03 |
| DuroTak 87-4287 | 73.97 | 73.78 | 73.62 |
| Methyl laurate | 10.04 | — | 9.98 |
| Ethyl laurate | — | 10.07 | — |
| Levulinic acid | 5.97 | 6.19 | 6.00 |
| Aluminium acetylacetonate | — | — | 0.37 |
| Area weight [g/m$^2$] | 134.1 | 130.7 | 128.3 |

Figure 6:
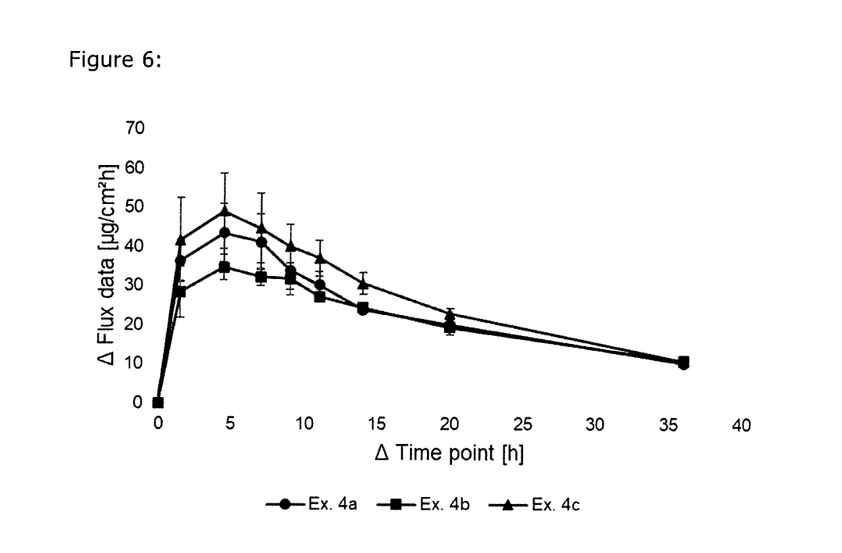
FIG. 6 is a graphical comparison of S-ketamine skin permeation compared to ethyl laurate and the usage of cross linking agent.

The skin permeation rate was determined analogously to Example 1 and is summarized in FIG. 6. The skin permeation of the examples shows that the cross linking agent Aluminium acetylacetonate does not influence the onset of flux and that methyl laurate is more advantageous than ethyl laurate regarding the onset of flux.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A transdermal therapeutic system comprising a backing layer which is not permeable for the active ingredient, and at least one matrix layer on one side of the backing layer, wherein the matrix layer includes at least one pressure sensitive adhesive comprising an acrylic copolymer including free hydroxyl groups and no free carboxyl groups, and (S)-ketamine or a pharmaceutically acceptable salt or solvate thereof, and a penetration enhancer comprising a mixture of levulinic acid and methyl laurate, wherein the matrix layer has an area weight of 100 to 275 g/m$^2$, wherein the methyl laurate is present in an amount greater than the levulinic acid, and wherein the weight ratio of levulinic acid to methyl laurate is between about 1:1.66 and 1:1.68.

2. The transdermal therapeutic system of claim 1, wherein the at least one pressure sensitive adhesive comprises an acrylic copolymer selected from 2-ethylhexyl acrylic acetate, vinyl acetate, and 2-hydroxyethyl acrylate.

3. The transdermal therapeutic system of claim 1, wherein the matrix layer comprises the penetration enhancers in an amount of about 1 to 15 wt.-%, based on the weight of the matrix layer and wherein each penetration enhancer is present in an amount of between about 4 and 10 wt. %.

4. The transdermal therapeutic system of claim 1, wherein the matrix layer comprises ketamine in an amount of about 1 to 25 wt.-%, based on the weight of the matrix layer.

5. The transdermal therapeutic system of claim 1, wherein the matrix layer comprises at least one antioxidant.

6. The transdermal therapeutic system of claim 5, wherein the at least one antioxidant is selected from the group consisting of alpha-tocopherol, ascorbyl, palmitate, dibutylhydroxy toluene, and mixtures thereof.

7. The transdermal therapeutic system of claim 1, wherein the transdermal therapeutic system comprises a detachable protective layer on the side of the matrix layer on which the backing layer is not arranged.

8. The transdermal therapeutic system of claim 1, wherein the pressure sensitive adhesive comprises between about 70 to 85 wt. % of an entirety of the matrix layer.

\* \* \* \* \*